US00PP31362P2

(12) United States Plant Patent
Horvath

(10) Patent No.: US PP31,362 P2
(45) Date of Patent: Jan. 14, 2020

(54) ***PENNISETUM ALOPECUROIDES* PLANT NAMED 'YELLOW RIBBONS'**

(50) Latin Name: *Pennisetum alopecuroides*
Varietal Denomination: Yellow Ribbons

(71) Applicant: Brent Horvath, Fontana, WI (US)

(72) Inventor: Brent Horvath, Fontana, WI (US)

( * ) Notice: Subject to any disclaimer, the term of this patent is extended or adjusted under 35 U.S.C. 154(b) by 0 days.

(21) Appl. No.: 16/350,650

(22) Filed: Dec. 17, 2018

(51) Int. Cl.
*A01H 5/00* (2018.01)

(52) U.S. Cl.
USPC ..... Plt./384

(58) Field of Classification Search
USPC ..... Plt./384
CPC ..... A01H 5/00
See application file for complete search history.

*Primary Examiner* — Annette H Para

(57) ABSTRACT

A new, distinct *Pennisetum alopecuroides* plant as shown and described, characterized by yellow foliage and yellow-green inflorescences on 50 cm stems that start in mid-August in northern Illinois.

2 Drawing Sheets

Figure 1:
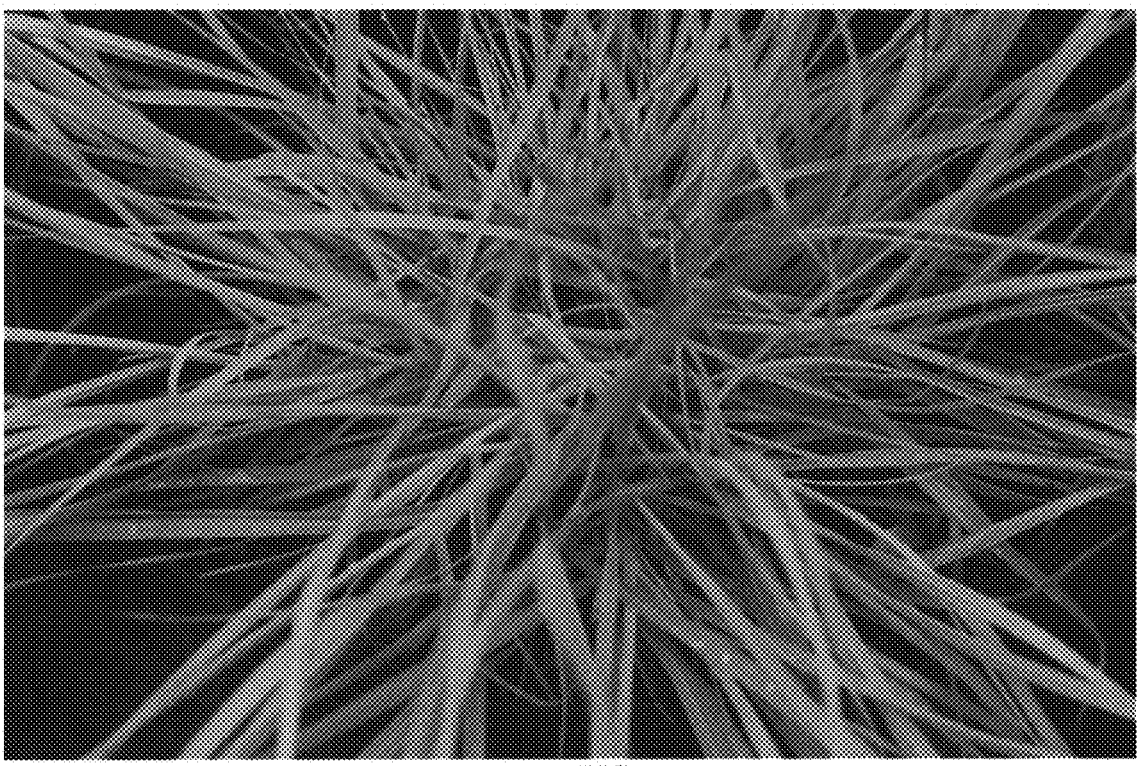

Latin name: *Pennisetum alopecuroides.*
Cultivar name: 'Yellow Ribbons'.

BACKGROUND OF THE INVENTION

The present invention relates to a new form of *Pennisetum alopecuroides* plant named 'Yellow Ribbons'. 'Yellow Ribbons' is a seedling of an unnamed *Pennisetum alopecuroides*, not patented, characterized by yellow foliage and yellow-green inflorescences on 50 cm stems that start in mid-August in northern Illinois. The new plant is the result of a breeding program taking place at a wholesale perennial nursery since 2001. The seedling was grown by the inventor at a wholesale perennial nursery in Hebron, Ill. in 2016. The selection of the new plant was due to its yellow foliage and yellow-green inflorescences on 50 cm stems that start in mid-August in northern Illinois. Asexual, vegetative division propagation has been the only means of reproduction. Propagation has taken place at a wholesale perennial nursery Hebron, Ill. in 2017. To date these plants have remained uniform in height. The new *Pennisetum* has shown to be stable and identical in reproduction to the parent after making over 500 vegetative divisions in 2018. No plants of the new *Pennisetum* have been sold in this country, or anywhere in the world, prior to the filing of this application, nor has any disclosure of the new plant been made prior to the filing of this application with the exception of that which was disclosed within one year of filing of this application and was either derived directly or indirectly for the inventor.

SUMMARY OF THE INVENTION

In the following description, color references are made to The Royal Horticultural Society Colour Chart. The new *Pennisetum alopecuroides* plant named 'Yellow Ribbons' has shown the characteristics of yellow foliage and yellow-green inflorescences on 50 cm stems that start in mid-August in northern Illinois.

The parent plants were not available for comparison. Plants of the new *Pennisetum* can be compared to plants of *Pennisetum alopecuroides* 'Red Head,' not patented. 1. The new *Pennisetum* has a height of 50 cm compared to the height of *Pennisetum alopecuroides* 'Red Head' which has a height of 120 cm. 2. The new Pennisetum has an inflorescence length of 9 cm compared to *Pennisetum alopecuroides* 'Red Head' which has an inflorescence length of 20 cm.

Plants of the new *Pennisetum* can be compared to plants of *Pennisetum alopecuroides* 'Hameln,' not patented. 1. The new *Pennisetum* has a height of 50 cm compared to the height of *Pennisetum alopecuroides* 'Hameln' which has a height of 90 cm. 2. The new *Pennisetum* has an inflorescence length of 9 cm compared to *Pennisetum alopecuroides* 'Hameln' which has an inflorescence length of 10 cm. 3. The new *Pennisetum* has a yellow foliage and yellow-green inflorescence color compared to *Pennisetum alopecuroides* 'Hameln' which has a tan inflorescence color.

Plants of the new *Pennisetum* can be compared to plants of *Pennisetum alopecuroides* 'Mondry,' not patented. 1. The new *Pennisetum* has a height of 50 cm compared to the height of *Pennisetum alopecuroides* 'Moudry' which has a height closer to 60 cm. 2. The new *Pennisetum* has a mid-August bloom time compared to *Pennisetum alopecuroides* 'Moudry' which typically blooms in October.

DESCRIPTION OF PHOTOGRAPHS

FIG. 1. Shows the golden foliage on a plant in Hebron, Ill. USA.

Figure 2:
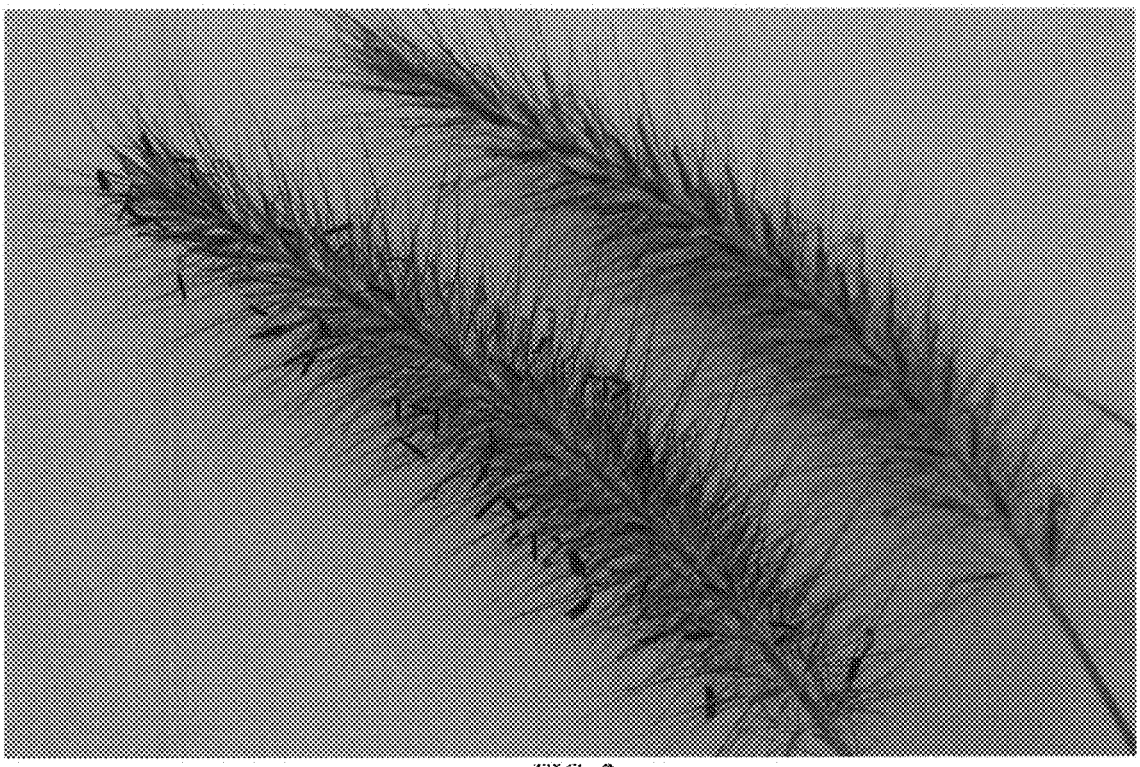

FIG. 2. Shows a close up of the flower in Hebron, Ill. USA.

Figure 3:
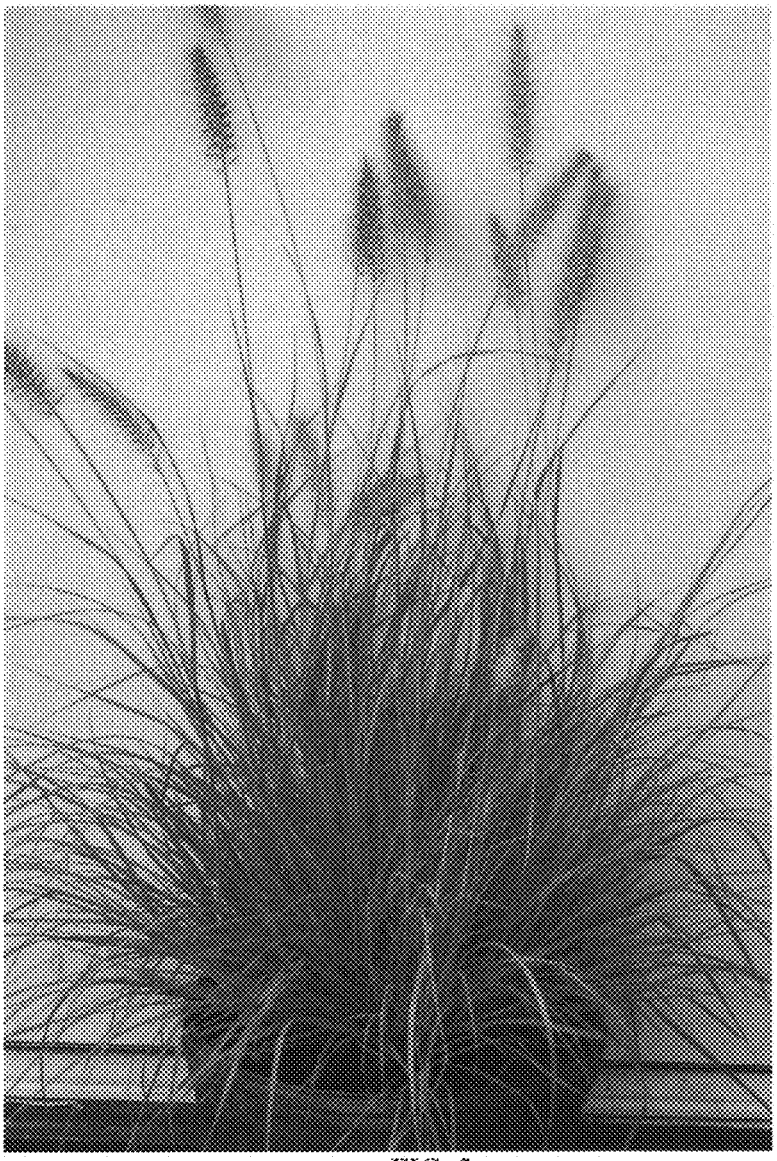

FIG. 3. Shows an entire plant blooming in August in Hebron, Ill. USA

DETAILED BOTANICAL DESCRIPTION

In the following description, color references are made to The Royal Horticultural Society Colour Chart (2001). The plant herein described is a one year old, three gallon specimen grown in full sun and irrigated in Hebron, Ill.

Botanical classification: *Pennisetum alopecuroides* cultivar 'Yellow Ribbons'.

Parentage: *Pennisetum alopecuroides* unnamed seedling selections.

Propagation: Vegetative division.

Plant description: Overall habit of the new *Pennisetum* is strongly clumping mounds with upright stems topped by yellow-green colored inflorescences in mid-August. Vigor is moderate to fast.

*Plant height.*—50 cm.

*Plant width.*—60 cm.

*Stem diameter.*—4 mm.

*Stem color.*—At the base 151 A; 155 D at the center; 146 C at the top.

Foliage:

*Type.*—Deciduous, grass growing in culms.

*Shape.*—Blade.

*Petiole.*—None.

*Blade length.*—27 cm average, ranging from 19-35 cm, Width — 5 mm.

*Immature adaxial leaf description.*—The leaf color is yellow-green color 151 C.

*Immature abaxial leaf description.*—The leaf color is yellow-green color 151 C.

*Mature adaxial leaf description.*—The leaf color is yellow-green color 146 B.

*Mature abaxial leaf description.*—The leaf color is yellow-green color 146 B.

*Basal Leaf sheath color.*—146 B.

*Leaf sheath.*—Glabrous.

*Auricles.*—Not present.

*Ligules.*—As wide as the leaf blade, 1 mm tall, color 146 B.

*Collars.*—Continuous, as wide as the leaf blade, less than 1 mm tall, color 146 B.

*Leafbuds.*—Folded in the bud stage.

*Rhizomes or stolons.*—None. The attitude of the tiller on the culm is erect, 45 degrees from the culm. The culm node is glabrous and color at the node is 146 B.

*Internode.*—Length 7-10 cm.

*Culm diameter and color at the internode.*—4 mm, close to 146 B.

*Fall leaf color.*—Mostly green 146 B with some 153 D fall color.

Flower inflorescence:

*Number of spike bearing tillers in the culmus.*—38.

*Inflorescence type.*—Terminal bristled spike.

*Floret color.*—153 A.

*Individual floret size.*—1 mm across, 7 mm tall.

*Anther coloration and size.*—N200 A, 4 mm long, 0.5 mm wide.

*Stigma color and size.*—Close to 153 A, 7 mm long, 1 mm wide.

*Glume color and size.*—Close to 153 A, 5 mm, less than 1 mm wide.

*Bristle size.*—20 mm long, less than 1 mm wide.

*Bristle color.*—165 A.

*Caryopsis color.*—153 A, shape — elliptic.

*Overall inflorescence spike size.*—3 cm wide, 12 cm long.

*Flower number.*—Approximately 125 florets per mature spike measuring 3 cm wide, 12 cm long.

*Fertility.*—Self-fertile, Fertile with 3 Anthers and 3 Stamens, 1 Stigma.

*Blooming habit.*—Terminal bristled spike on up to 63 cm stems.

*Bloom period and duration.*—Mid-August into October.

*Scent.*—No scent noticed.

*Bloom color overall.*—153 A.

*Roots.*—Stiff, fibrous, and freely branching.

*Fruit.*—Seed identical to the species except size is a slightly smaller. Color 153 A.

*Disease resistance.*—Plants are not susceptible to any major pests or diseases.

I claim:

1. A new and distinct variety of *Pennisetum alopecuroides* plant named 'Yellow Ribbons' as illustrated and described, characterized by yellow foliage and yellow-green inflorescences on 50 cm stems that start in mid-August in northern Illinois.

* * * * *